(12) United States Patent
Ching

(10) Patent No.: US 8,400,741 B1
(45) Date of Patent: Mar. 19, 2013

(54) PROGRAMMABLE ECHO SIGNAL SWITCH WITH T/R SWITCH FOR ULTRASOUND BEAMFORMING INTEGRATED CIRCUIT AND METHOD

(75) Inventor: Chu Ching, San Jose, CA (US)

(73) Assignee: Supertex, Inc., Sunnyvale, CA (US)

( * ) Notice: Subject to any disclaimer, the term of this patent is extended or adjusted under 35 U.S.C. 154(b) by 244 days.

(21) Appl. No.: 12/793,355

(22) Filed: Jun. 3, 2010

Related U.S. Application Data

(60) Provisional application No. 61/347,756, filed on May 24, 2010.

(51) Int. Cl.
*H02H 3/22* (2006.01)

(52) U.S. Cl. .......................................... 361/56; 361/111

(58) Field of Classification Search .................... 361/56, 361/111
See application file for complete search history.

(56) References Cited

U.S. PATENT DOCUMENTS

| | | | |
|---|---|---|---|
| 5,200,876 A * | 4/1993 | Takeda et al. ................... 361/56 |
| 2004/0000841 A1* | 1/2004 | Phelps et al. .................. 310/314 |
| 2005/0146371 A1* | 7/2005 | Wodnicki ...................... 327/382 |
| 2009/0052099 A1* | 2/2009 | Chee et al. ..................... 361/56 |
| 2010/0152587 A1* | 6/2010 | Haider et al. ................. 600/459 |

* cited by examiner

*Primary Examiner* — Danny Nguyen
(74) *Attorney, Agent, or Firm* — Weiss & Moy, P.C.; Jeffrey D. Moy

(57) ABSTRACT

An electrical switching array and method uses a programmable multi-channel analog switch with a high voltage T/R switch and voltage limiting circuit for ultrasound image system echo signal multiplexing beamforming receiver frontend circuit.

12 Claims, 3 Drawing Sheets

PROGRAMMABLE ECHO SIGNAL SWITCH WITH T/R SWITCH FOR ULTRASOUND BEAMFORMING INTEGRATED CIRCUIT AND METHOD

RELATED APPLICATIONS

The present application claims the benefit to and is related herewith to U.S. Provisional Application entitled, "PROGRAMMABLE ECHO SIGNAL MULTIPLEXER WITH T/R SWITCH FOR ULTRASOUND BEAMFORMING INTEGRATED CIRCUIT AND METHOD", filed May 24, 2010, and having U.S. Ser. No. 61/347,756 in the name of the same inventor, and which is incorporated herein by reference in its entirety.

FIELD OF THE INVENTION

This invention relates to an ultrasound beamformer circuit and, more specifically, to a programmable multi-channel analog switch with a high voltage T/R switch and voltage limiting circuit for an ultrasound image system echo signal multiplexing beamforming receiver frontend circuit.

BACKGROUND OF THE INVENTION

Medical or nondestructive testing (NDT) ultrasound imaging applications have a growing demand for more sophisticated echo signal beamforming in the receiver frontend circuit. This may be necessary to generate high resolution acoustic images. The conventional ultrasound echo multiplexing circuits usually have an array of high-voltage analog switches (MUX) in between a transducer probe PZT array and multiple Tx/Rx channel circuitry.

These circuits have several limitations. These circuits first require Tx and Rx channel having an equal number of channels. Second, the transmitting pulses are generally high voltage and the receiving echo signals are generally low voltage. However, both signals have to pass through the same MUX. This requires that every MUX switch must have a low on-resistance when its turned on, and that it can withstand high voltage when it is turned off. These requirements make the cost of the MUX switch very high.

Therefore, it would be desirable to provide a circuit and method that overcomes the above problems. The circuit and method would be able to switch the echo signal only to overcome the above problems.

SUMMARY

In accordance with one embodiment, an electrical switching array circuit has at least one switching circuit. A control interface is coupled to the at least one switching circuit to activate and deactivate the at least one switching circuit. A high-voltage Transmit/Receive (T/R) switch is coupled to the at least one switching circuit. A clamping circuit is coupled to the at least one switching circuit and the high-voltage T/R switch.

In accordance with one embodiment, a protection circuit for a switch array circuit has a programmable on/off control digital interface. A high-voltage transmit/receive (T/R) switch is connected at an input terminal of the switch array circuit. A voltage limiting circuit is connected to the input terminal of the switch array circuit.

The present invention will be more apparent from the following detailed description taken in conjunction with the accompanying drawings.

BRIEF DESCRIPTION OF THE DRAWINGS

Common reference numerals are used throughout the drawings and detailed description to indicate like elements.

DETAILED DESCRIPTION

In the present invention, a digital programmable, low voltage analog switch, diode voltage clamping circuit and high voltage T/R switch circuit provides an ultrasound imaging system an echo receiving frontend suitable for large number array transducer elements of electronics controlled dynamic focus, acoustic phase-array, and receiving beamforming technology, which may be used in color Doppler image portable ultrasound machines. In various embodiments, the digital programmable, low voltage analog switch, diode voltage clamping circuit and high voltage T/R switch circuit channels are integrated into very small ICs.

Figure 1:
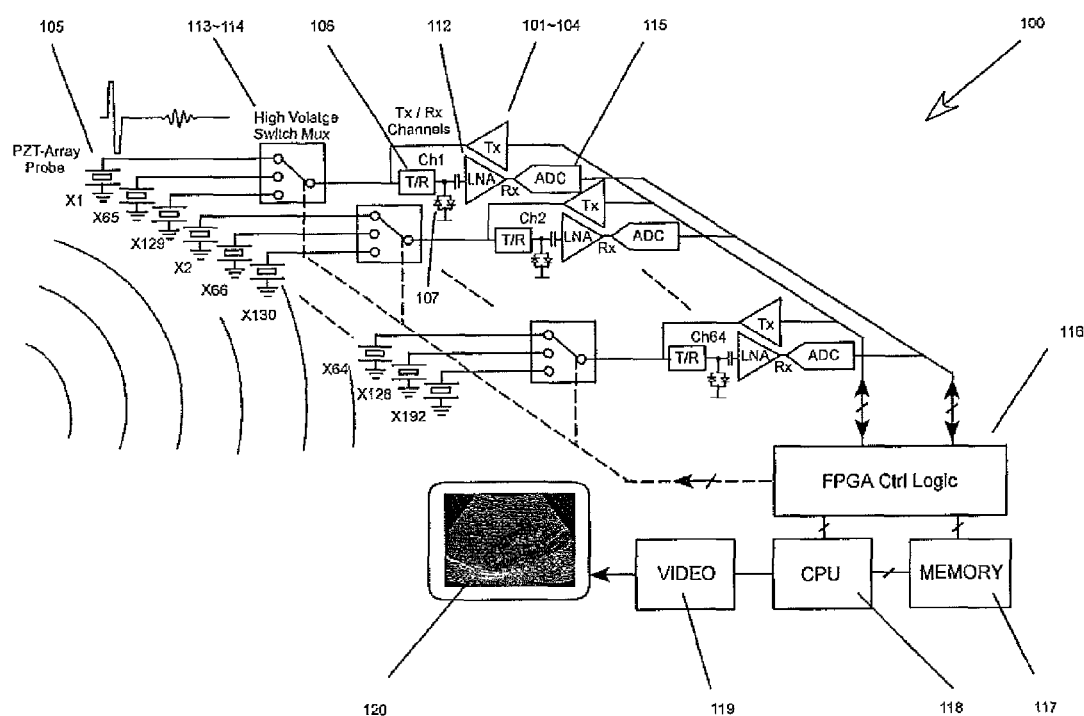
FIG. 1 is a prior art schematic diagram illustrating a conventional high voltage (HV) analog multiplexer for an ultrasound image system with 64-channel of transmit/receive (Tx/Rx) and 192-element array probe transducer.

Referring to FIG. 1, an ultrasound image system 100 of the prior art is shown. The schematic diagram of the ultrasound image system 100 illustrates a conventional high voltage analog switch multiplexer with 64-channel of Tx/Rx and 192-element array probe transducer.

In operation, the multiple channels of Tx pulser 101 send bipolar or unipolar high voltage excitation pulses, through high voltage T/R switches 106 and multiplexing switch 113, to the PZT-array probe transducers 105. The Tx pulses peak to peak voltage may be between anywhere from +/−2V to +/−150V. The low voltage echo signals received by the same or different PZT elements 105, then through the switches 113 and 106 back into the receiver channel LNA 112 and ADC 115.

Usually the peak to peak voltage of the echo signal is only about +/−0.8V to as small as few micro-volts. The echo signals then being processed by the digital rear side FPGA interface 116, CPU 118 and data memory 117 then through video circuit send to display 120 and an acoustic image. This is the prior arts of conventional ultrasound image system architecture of configuration.

Figure 2:
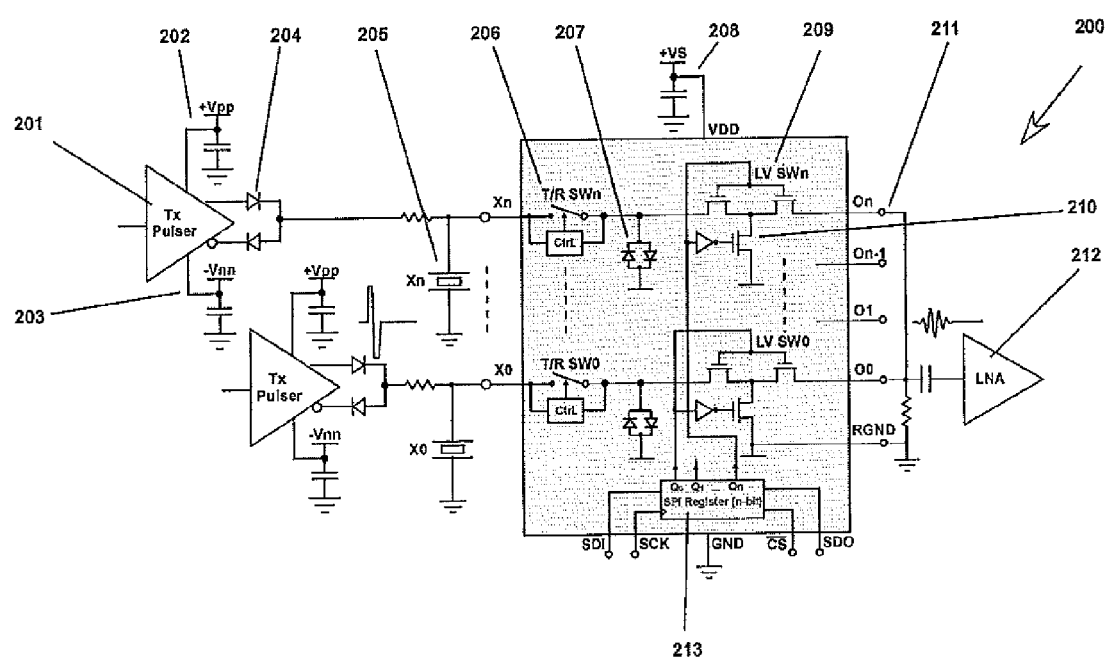
FIG. 2 is a schematic diagram illustrating a low voltage analog switch array with diode clamping and high voltage T/R switches accordance with one embodiment of the present invention.

Referring now to FIG. 2, a schematic block diagram illustrating an ultrasound image system 200 is shown. The ultrasound image system 200 has a plurality of low-voltage receive beamforming analog switch circuits 209 (hereinafter low voltage switches 209). The low voltage switches 209 may be comprised of a pair of MOSFET transistors 209A and 209B. The input of each of the low voltage switches 209 is connected to a respective clamping circuit 207 and to a respective output of a T/R switch 206. In accordance with one embodiment, the clamping circuit 207 is comprised of a pair of diodes 207A and 207B.

The outputs of the low voltage switches 209 are selectively connected through package lead 211 to a Low Noise Amplifiers (LNA) 212. A serial digital or serial peripheral interface (SPI) circuit 213 is coupled to each of the low voltage switches 209 and provides programmable means to control the low voltage switches 209.

A plurality of transmit (Tx) pulser 201 is each powered by VPP and VNN high voltage supplies 202 and 203. The output of each of the Tx pulsers 201 are coupled through isolation diodes 204 and an impedance-matching resistor 215, connected to an array PZT element 205. The array PZT element 205 is also connected to the input of the array of high voltage T/R switches 209.

The T/R switch 206 is a two-terminal voltage controlled normally-on switch. During the high voltage Tx pulse 201 existing period, the T/R switch 206 is off or in very high impedance state. The diodes back-to-back clamping circuit 207 provides LV switch input voltage limits against any leakage of the T/R switch 206. It makes sure the input of the low voltage switch 209 will always be within about a peak-to-peak diode drop, which usually is in the range of approximately +/−0.5 to +/−1.2V of the voltages. The useful echo signals usually are only few hundred mV to µV range. Therefore, the array of the low voltage switches 209 only needs work at a very low input voltages range.

A MOSFET "T" switch 210 is connected to a middle point of the main MOSFET switch 209B of the low voltage switch 209, to increase the off-isolation of the low voltage switch 209 in a high-frequency (RE) range. When the main MOSFET switches in the low voltage switch 209 are turned on, the "T" switch 210 is off, when the low voltage switch 209 is off the switch 210 will be on.

All low voltage switches 209 are controlled by the outputs of a serial register Q0~Qn in 213.

Figure 3:
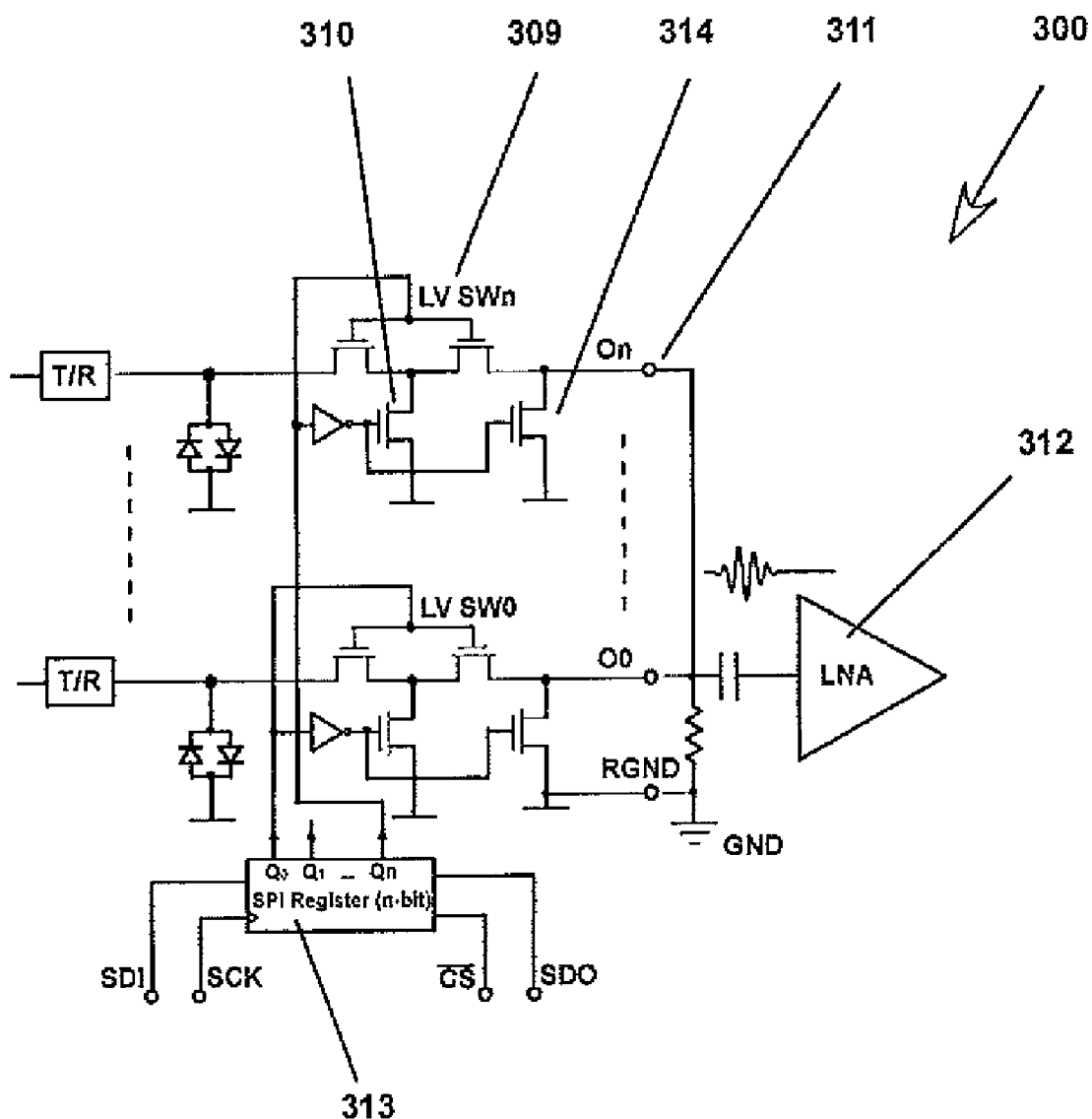
FIG. 3 is a schematic diagram illustrating a low voltage analog switch with additional output damping switch.

Referring to FIG. 3, an additional analog switch 314 is connected to the output of the low voltage switch 209 and to ground. The additional analog switch 314 may be used to provide additional low impedance damping path for the output and LNA input circuits 312, on each channel 311.

This disclosure provides exemplary embodiments of the present invention. The scope of the present invention is not limited by these exemplary embodiments. Numerous variations, whether explicitly provided for by the specification or implied by the specification, such as variations in structure, dimension, type of material and manufacturing process, may be implemented by one skilled in the art in view of this disclosure.

What is claimed is:

1. An electrical switching array circuit comprising:
   at least one switching circuit;
   a T switch coupled to the at least one switching circuit to increase an off-isolation of the at least one switching circuit;
   a control interface coupled to the at least one switching circuit to activate and deactivate the at least one switching circuit;
   a high-voltage Transmit/Receive (T/R) switch coupled to the at least one switching circuit; and
   a clamping circuit coupled to the at least one switching circuit and the high-voltage T/R switch.

2. An electrical switching array comprising:
   at least one switching circuit;
   a control interface coupled to the at least one switching circuit to activate and deactivate the at least one switching circuit;
   a high-voltage Transmit/Receive (T/R) switch coupled to the at least one switching circuit;
   a clamping circuit coupled to the at least one switching circuit and the high-voltage T/R switch; and
   a damping switch coupled to an output of the at least one switching circuit and to the ground.

3. An electrical switching array in accordance with claim 1 wherein the at least one switching circuit is a two terminal normally-on switch.

4. An electrical switching array in accordance with claim 1 wherein the at least one switching circuit comprises a pair of MOSFET transistors.

5. An electrical switching array in accordance with claim 1 wherein the clamping circuit comprises a pair of diodes.

6. A protection circuit for a switch array circuit comprising:
   a programmable on/off control digital interface;
   a high-voltage transmit/receive (T/R) switch connected at an input terminal of the switch array circuit;
   a voltage limiting circuit connected to the input terminal of the switch array circuit; and
   an analog "T" switch coupled to the switch array circuit and ground.

7. A protection circuit for a switch array circuit comprising:
   a programmable on/off control digital interface;
   a high-voltage transmit/receive (T/R) switch connected at an input terminal of the switch array circuit;
   a voltage limiting circuit connected to the input terminal of the switch array circuit; and
   an analog damping switch coupled to an output of the switch array circuit and ground.

8. A protection circuit for an integrated electrical switch circuit comprising:
   a programmable on/off control digital interface;
   a plurality of high-voltage Transmit/Receive (T/R) switches connect at an input of the switch circuit;
   a plurality of voltage limiting circuits connect at the input of the switch circuit; and
   a plurality of "T" switches coupled to the switch circuit and to ground.

9. A protection circuit for an integrated electrical switch circuit comprising:
   a programmable on/off control digital interface;
   a plurality of high-voltage Transmit/Receive (T/R) switches connect at an input of the switch circuit;
   a plurality of voltage limiting circuits connect at the input of the switch circuit; and
   a plurality of damping switches coupled to the switch circuit and to ground.

10. An electrical switching array in accordance with claim 2 wherein the at least one switching circuit is a two terminal normally-on switch.

11. An electrical switching array in accordance with claim 2 wherein the at least one switching circuit comprises a pair of MOSFET transistors.

12. An electrical switching array in accordance with claim 2 wherein the clamping circuit comprises a pair of diodes.

* * * * *